United States Patent
Kumar et al.

(10) Patent No.: US 10,060,864 B2
(45) Date of Patent: Aug. 28, 2018

(54) MULTI-SAMPLING IN X-RAY RECEIVER FOR NOISE REDUCTION

(71) Applicant: Texas Instruments Incorporated, Dallas, TX (US)

(72) Inventors: Goli Sravana Kumar, Bengaluru (IN); Nagesh Surendranath, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/900,621

(22) Filed: Feb. 20, 2018

(65) Prior Publication Data

US 2018/0180559 A1 Jun. 28, 2018

Related U.S. Application Data

(63) Continuation of application No. 14/658,291, filed on Mar. 16, 2015.

(30) Foreign Application Priority Data

Mar. 20, 2014 (IN) .......................... 1497/CHE/2014

(51) Int. Cl.
*G01N 23/04* (2018.01)
*H04N 5/357* (2011.01)
*H04N 5/378* (2011.01)
*H04N 5/32* (2006.01)
*A61B 6/00* (2006.01)

(52) U.S. Cl.
CPC .............. *G01N 23/04* (2013.01); *A61B 6/42* (2013.01); *H04N 5/32* (2013.01); *H04N 5/3575* (2013.01); *H04N 5/378* (2013.01)

(58) Field of Classification Search
CPC .......... G01N 23/04; H04N 5/32; H04N 5/357; H04N 5/3575; H04N 5/378; A61B 6/42; G01T 1/17; G01T 1/247
See application file for complete search history.

(56) References Cited

U.S. PATENT DOCUMENTS

2013/0113461 A1* 5/2013 Mantri ................... H04N 5/359
                                                                    324/103 R
2014/0049291 A1* 2/2014 Soh .......................... H03K 5/00
                                                                    327/94

OTHER PUBLICATIONS

Prosecution History from U.S. Appl. No. 14/658,291, dated Mar. 16, 2015 to Nov. 20, 2017, 104 pp.

* cited by examiner

*Primary Examiner* — Glen Kao
(74) *Attorney, Agent, or Firm* — Gregory J. Albin; Charles A. Brill; Frank D. Cimino

(57) ABSTRACT

The disclosure provides a receiver with reduced noise. The receiver includes a photodiode that generates an input signal in response to received light pulses. A pixel switch is coupled to the photodiode. An operational amplifier is coupled to the photodiode through the pixel switch. A feedback capacitor and a reset switch are coupled between a first input port and an output port of the operational amplifier. A switched resistor network is coupled to the output port of the operational amplifier. A first switched capacitor network is coupled to the switched resistor network and samples a reset voltage. A second switched capacitor network is coupled to the switched resistor network and samples a signal voltage. A subtractor receives the reset voltage and the signal voltage, and generates a sample voltage. The second switched network comprises two or more capacitors.

26 Claims, 5 Drawing Sheets

MULTI-SAMPLING IN X-RAY RECEIVER FOR NOISE REDUCTION

CROSS REFERENCES TO RELATED APPLICATIONS

This application is a continuation of U.S. patent application Ser. No. 14/658,291, filed on Mar. 16, 2015, and claims priority to India provisional patent application No. 1497/CHE/2014 filed on Mar. 20, 2014, both of which are hereby incorporated by reference in their entirety.

TECHNICAL FIELD

The present disclosure is generally related to sampling circuits, and more particularly to correlated multi-sampling in x-ray receiver for flicker noise reduction.

BACKGROUND

An x-ray system is a useful diagnostic tool in a wide variety of applications. In medical applications, x-ray detection is used to capture images representing parts of a patient's body. These images are used for diagnosis and treatment. In industrial applications, x-rays are used to detect defects in pipes, aircrafts, material testing. x-ray systems also find applications in spectroscopy for particle composition of an object under test.

An x-ray system includes an x-ray source that generates x-rays. The x-rays are emitted towards an object. The object is any entity of interest which may include, but not limited to, a human, an automated component, an animal, a device etc. The x-rays pass through the object to generate light pulses.

The x-ray system includes an analog front end receiver that includes a plurality of receivers. A receiver of the plurality of receivers receives the light pulses. The receiver includes a feedback capacitor and an operational amplifier. The feedback capacitor in the receiver stores a charge corresponding to the intensity of the light pulses. At the start of each frame of received light pulse, a reset is provided to the feedback capacitor. This introduces a reset phase noise in the receiver.

In addition, a flicker noise which is a low frequency noise is introduced because of the operational amplifier. The noises (reset phase noise and flicker noise) distort processing of light pulses in the receiver. This causes a low quality of image/data produced by the x-ray system.

SUMMARY

According to an aspect of the disclosure, a receiver is disclosed. The receiver includes a photodiode that generates an input signal in response to received light pulses. A pixel switch is coupled to the photodiode. An operational amplifier is coupled to the photodiode through the pixel switch. A feedback capacitor and a reset switch are coupled between a first input port and an output port of the operational amplifier. A switched resistor network is coupled to the output port of the operational amplifier. A first switched capacitor network is coupled to the switched resistor network and samples a reset voltage. A second switched capacitor network is coupled to the switched resistor network and samples a signal voltage. A subtractor receives the reset voltage and the signal voltage, and generates a sample voltage. The second switched network comprises two or more capacitors.

BRIEF DESCRIPTION OF THE VIEWS OF DRAWINGS

Figure 1:
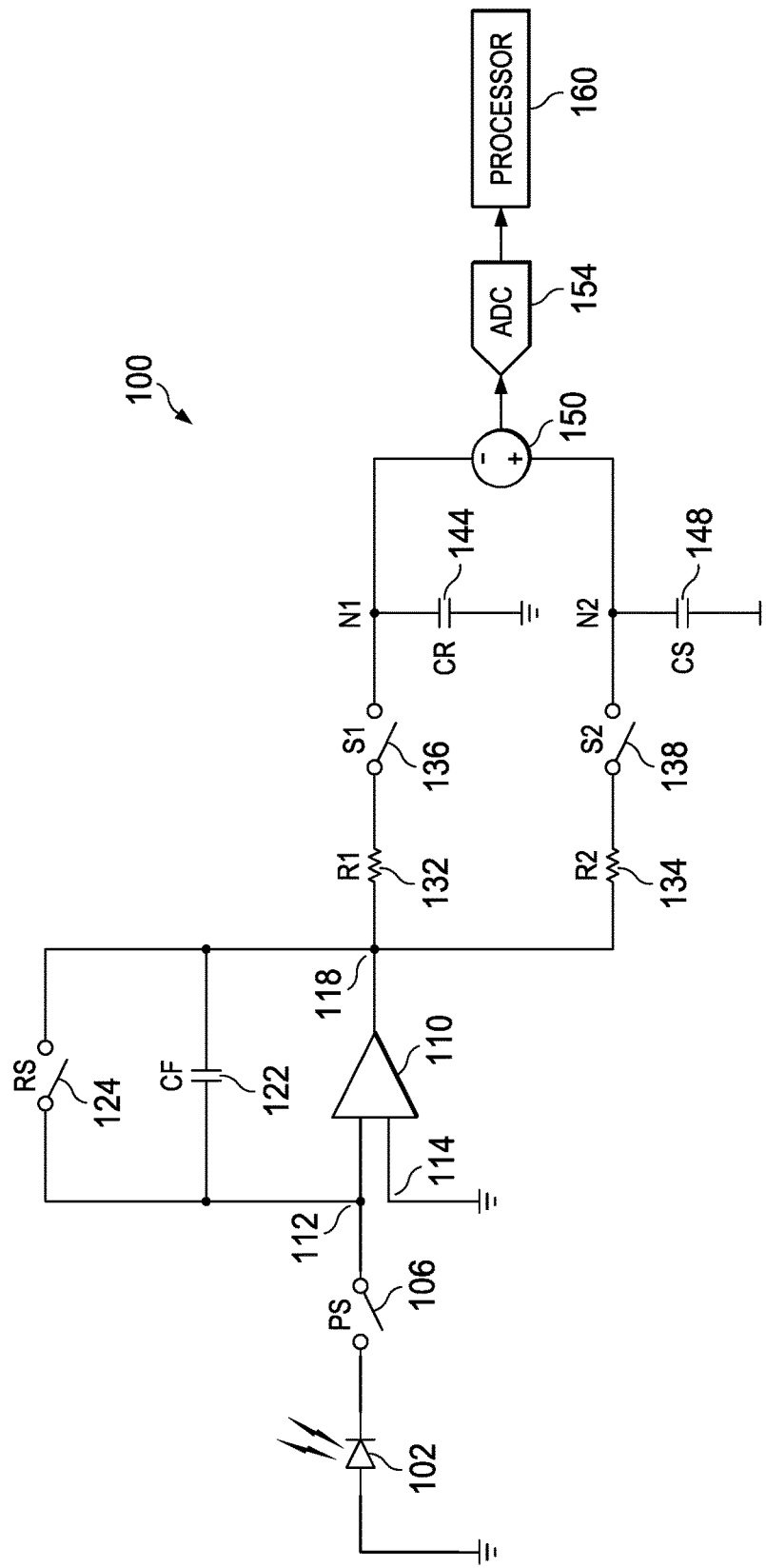
Figure 2:
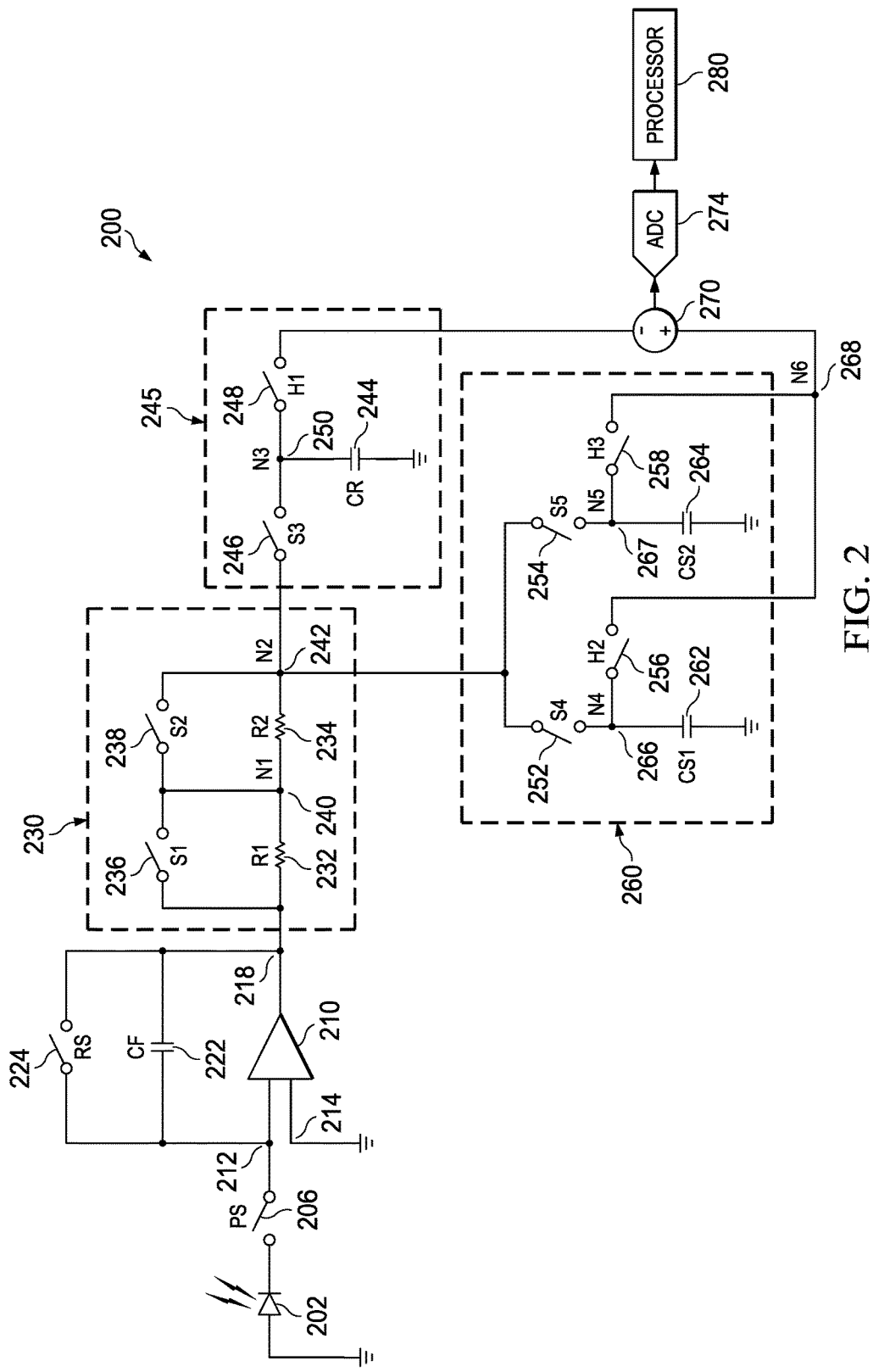
Figure 3:
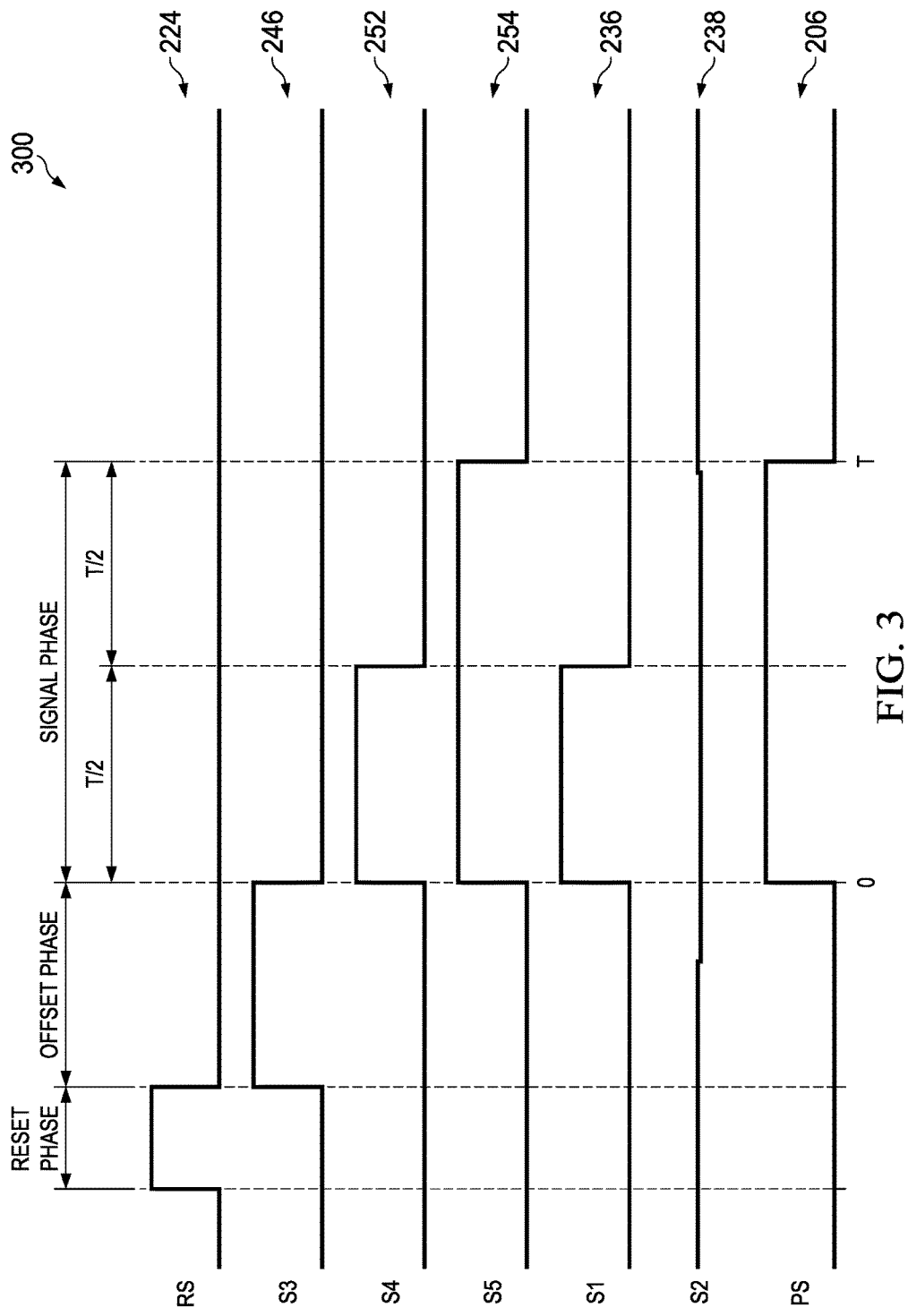
Figure 4:
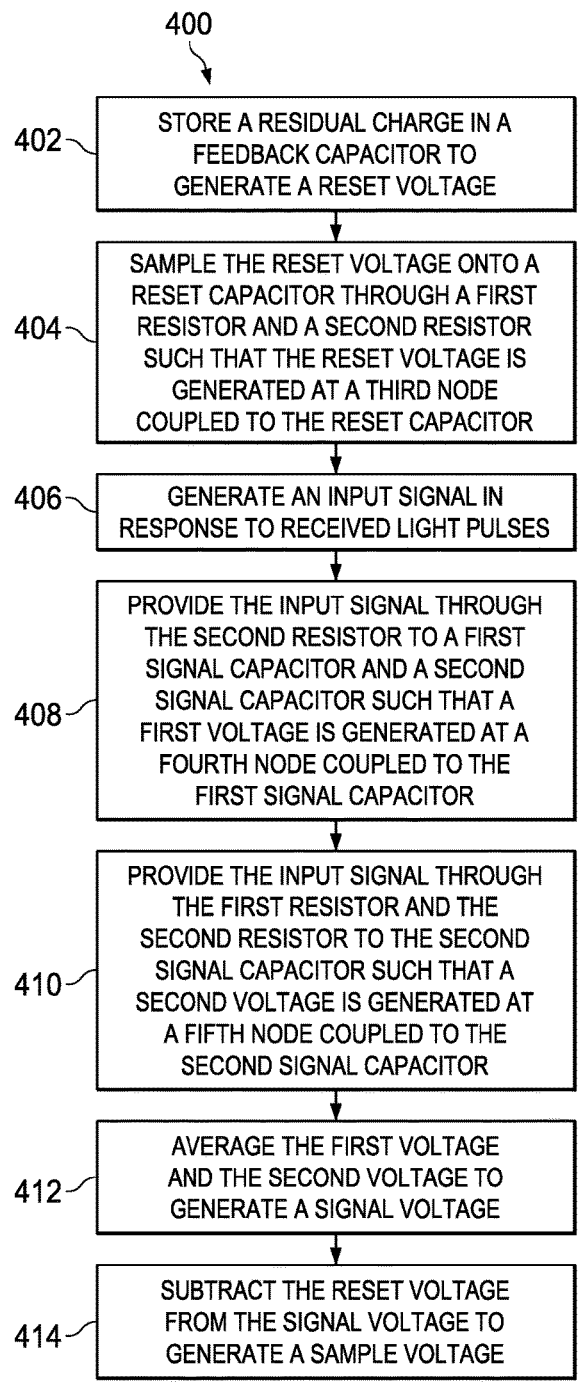
Figure 6:
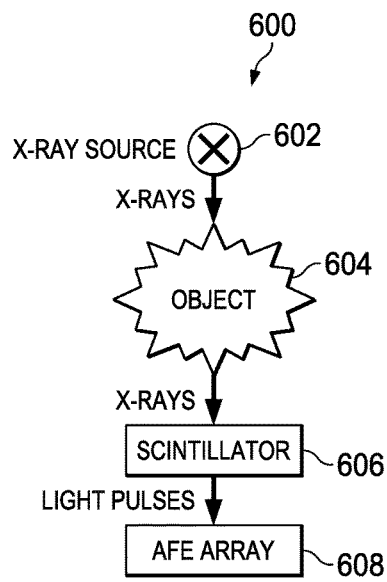
Figure 5:
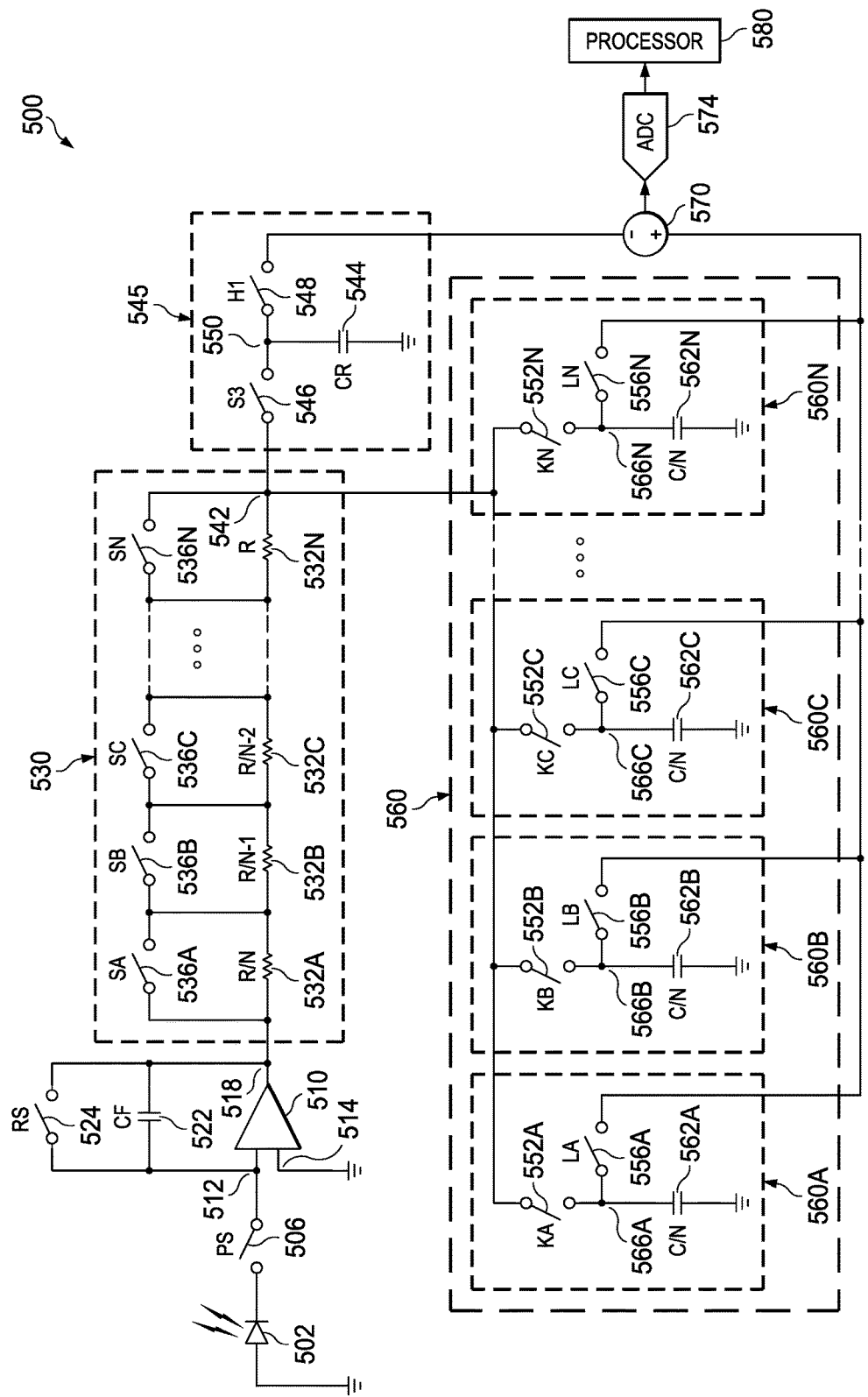

FIG. 1 illustrates a receiver;
FIG. 2 illustrates a receiver, according to an embodiment;
FIG. 3 illustrates a timing diagram for the receiver illustrated in FIG. 2, according to an embodiment;
FIG. 4 illustrates a method, according to an embodiment;
FIG. 5 illustrates a receiver, according to an embodiment; and
FIG. 6 illustrates an x-ray system, according to an embodiment.

DETAILED DESCRIPTION OF THE EMBODIMENTS

FIG. 1 illustrates a receiver 100. The receiver 100 includes a photodiode 102, an operational amplifier 110, a reset capacitor CR 144 and a signal capacitor CS 148, a subtractor 150, an analog to digital converter (ADC) 154 and a processor 160. A pixel switch PS 106 is coupled to the photodiode 102. The operational amplifier 110 is coupled to the photodiode 102 through the pixel switch PS 106.

A feedback capacitor CF 122 and a reset switch RS 124 are coupled between a first input port 112 and an output port 118 of the operational amplifier 110. A second input port 114 of the operational amplifier 110 is coupled to a ground terminal. A first resistor R1 132 and a second resistor R2 134 are coupled to the output port 118 of the operational amplifier 110.

The reset capacitor CR 144 is coupled to the first resistor R1 132 through a first switch S1 136. The signal capacitor CS 148 is coupled to the second resistor R2 134 through a second switch S2 138. The subtractor 150 is coupled to the reset capacitor CR 144 and the signal capacitor CS 148. The ADC 154 is coupled to the subtractor 150, and the processor 160 is coupled to the ADC 154.

The operation of the receiver 100 illustrated in FIG. 1 is explained now. The receiver 100 operates in a reset phase, an offset phase and a signal phase. In the reset phase, the pixel switch PS 106, the first switch S1 136 and the second switch S2 138 are opened, and the reset switch RS 124 is closed.

In the offset phase, the reset switch RS 124 is opened such that a residual charge is stored in the feedback capacitor CF 122. The residual charge creates a reset voltage at the output port 118 of the operational amplifier 110. The pixel switch PS 106, the reset switch RS 124 and the second switch S2 138 remain open while the first switch S1 136 is closed.

The reset voltage created at the output port 118 of the operational amplifier 110 is sampled onto the reset capacitor CR 144. Thus, the reset voltage is generated at a first node N1. In the signal phase, the reset switch RS 124 and the first switch S1 136 are opened. The pixel switch PS 106 and the second switch S2 138 are closed.

The photodiode 102 generates an input signal in response to received light pulses. The input signal from the photodiode 102 is received at the signal capacitor CS 148 such that a signal voltage is generated at a second node N2. The subtractor 150 receives the reset voltage generated at the first node N1, and the signal voltage generated at the second node N2.

The subtractor 150 subtracts the reset voltage from the signal voltage to generate a sample voltage. The ADC 154 generates a digital voltage in response to the sample voltage, and the processor 160 processes the digital voltage received from the ADC 154.

The residual charge stored during the offset phase is because of reset phase noise in the receiver 100. The receiver 100 is reset before a start of each frame. A frame spans for a frame time (T). This introduces the reset phase noise in the receiver 100. However, in the offset phase, the reset voltage generated at the first node N1 corresponds to the reset phase noise. Also, in the signal phase, the signal voltage generated at the second node N2 corresponds to the reset phase noise and a voltage generated from the light pulses received at the photodiode 102.

Thus, the reset phase noise is cancelled in the subtractor 150, and the sample voltage represent the voltage generated from the light pulses received at the photodiode 102. Also, any noise in the receiver 100 (for example, the flicker noise which is a low frequency noise and introduced because of the operational amplifier 110) whose frequency is less than a small fraction of 1/T is common in the reset voltage and the signal voltage. Such noise gets eliminated by the subtractor 150.

In some applications, the frame time (T) is selected to be more than a time required for settling of signal. The additional time is used to filter the thermal noise in the receiver 100. But, as the frame time (T) is increased, the flicker noise in the reset voltage and the signal voltage becomes uncorrelated and hence, dominates the noise at an output of the subtractor 150.

FIG. 2 illustrates a receiver 200, according to an embodiment. The receiver 200 includes a photodiode 202, an operational amplifier 210, a switched resistor network 230, a first switched capacitor network 245, a second switched capacitor network 260, a subtractor 270, an analog to digital converter (ADC) 274 and a processor 280.

A pixel switch PS 206 is coupled to the photodiode 202. The operational amplifier 210 is coupled to the photodiode 202 through the pixel switch PS 206. A feedback capacitor CF 222 and a reset switch RS 224 are coupled between a first input port 212 and an output port 218 of the operational amplifier 210. A second input port 214 of the operational amplifier 210 is coupled to a ground terminal.

The switched resistor network 230 is coupled to the output port 218 of the operational amplifier 210. The switched resistor network 230 includes a first resistor R1 232 and a second resistor R2 234. The first resistor R1 232 is coupled between the output port of the operational amplifier 210 and a first node N1 240. The second resistor R2 234 is coupled between the first node and a second node N2 242. The second resistor R2 234 is coupled to the first resistor R1 232 at the first node N1 240 serially. In one example, the resistance of the first resistor R1 232 and the second resistor R2 234 are equal.

A first switch S1 236 is coupled in parallel to the first resistor R1 232 between the output port 218 of the operational amplifier 210 and the first node N1 240. A second switch S2 238 is coupled in parallel to the second resistor R2 234 between the first node N1 240 and the second node N2 242. The first switched capacitor network 245 is coupled to the switched resistor network 230.

The first switched capacitor network 245 includes a third switch S3 246 coupled between the second node N2 242 and a third node N3 250. A reset capacitor CR 244 is coupled to the third switch S3 246 at the third node N3 250. One end of the reset capacitor CR 244 is coupled to a ground terminal. A first hold switch H1 248 is coupled between the third node N3 250 and the subtractor 270.

The second switched capacitor network 260 is coupled to the switched resistor network 230. The second switched capacitor network 260 includes a fourth switch S4 252 coupled between the second node N2 242 and a fourth node N4 266. A first signal capacitor CS1 262 is coupled to the fourth switch S4 252 at the fourth node N4 266. One end of the first signal capacitor CS1 262 is coupled to the ground terminal.

A fifth switch S5 254 is coupled between the second node N2 242 and a fifth node N5 267. A second signal capacitor CS2 264 is coupled to the fifth switch S5 254 at the fifth node N5 267. One end of the second signal capacitor CS2 264 is coupled to the ground terminal. A second hold switch H2 256 is coupled between the fourth node N4 266 and a sixth node N6 268. A third hold switch H3 258 is coupled between the fifth node N5 267 and sixth node N6 268.

In one version, a capacitance of the first signal capacitor CS1 262 and the second signal capacitor CS2 264 are equal. In another version, a sum of capacitance of the first signal capacitor CS1 262 and the second signal capacitor CS2 264 is equal to a capacitance of the reset capacitor CR 244.

The subtractor 270 is coupled to the third node N3 250 and the sixth node N6 268. The ADC 274 is coupled to the subtractor 270, and the processor 280 is coupled to the ADC 274. The receiver 200 may include one or more additional components known to those skilled in the relevant art and are not discussed here for simplicity of the description.

The operation of the receiver 200 illustrated in FIG. 2 is explained now. The receiver 200 operates in a reset phase, an offset phase and a signal phase. In the reset phase, the pixel switch PS 206, the third switch S3 246, the fourth switch S4 252 and the fifth switch S5 254 are opened. The reset switch RS 224 is closed.

In the offset phase, the reset switch RS 224 is opened such that a residual charge is stored in the feedback capacitor CF 222. The residual charge creates a reset voltage at the output port 218 of the operational amplifier 210. The pixel switch PS 206, the reset switch RS 224, the first switch S1 236, the second switch S2 238, the fourth switch S4 252 and the fifth switch S5 254 remain open while the third switch S3 246 is closed.

The reset voltage created at the output port 218 of the operational amplifier 210 is sampled onto the reset capacitor CR 244. Thus, the reset voltage is generated at the third node N3 250. In the signal phase, the reset switch RS 224, the second switch S2 238, the third switch S3 246, the first hold switch H1 248, the second hold switch H2 256, the third hold switch H3 258 are opened. The pixel switch PS 206, the first switch S1 236, the fourth switch S4 252 and the fifth switch S5 254 are closed.

The photodiode 202 generates an input signal in response to the received light pulses. In one example, the input signal is a charge signal. In another example, the input signal is a current signal. The input signal from the photodiode 202 is received at the first signal capacitor CS1 262 and the second signal capacitor CS2 264 through the second resistor R2 234. A voltage generated at the fourth node N4 266 is a first voltage.

The reset switch RS 224, the first switch S1 236, the second switch S2 238, the third switch S3 246, the fourth switch S4 252, the first hold switch H1 248, the second hold switch H2 256, the third hold switch H3 258 are opened. The pixel switch PS 206 and the fifth switch S5 254 are closed such that the input signal from the photodiode 202 is received at the second signal capacitor CS2 264 through the first resistor R1 232 and the second resistor R2 234. A corresponding voltage generated at the fifth node N5 267 is a second voltage.

After the signal phase, the third switch S3 246, the fourth switch S4 266 and the fifth switch S5 254 are opened. The first hold switch H1 248 is closed such that the reset voltage generated at the third node N3 250 is provided to the subtractor 270. The second hold switch H2 256 and the third hold switch H3 258 are closed such that the first voltage and the second voltage are averaged to generate the signal voltage.

Therefore, the first switched capacitor network 245 samples the reset voltage, and the second switched capacitor network 260 samples the signal voltage. The subtractor 270 receives the reset voltage and the signal voltage, and generates a sample voltage. In one example, the subtractor 270 subtracts the reset voltage from the signal voltage and generates the sample voltage.

The ADC 274 generates a digital voltage in response to the sample voltage, and the processor 280 processes the digital voltage received from the ADC 274.

The residual charge stored during the offset phase is because of reset phase noise in the receiver 200. The receiver 200 is reset before a start of each frame. A frame spans for a frame time (T). This introduces the reset phase noise in the receiver 200. However, in the offset phase, the reset voltage generated at the third node N3 250 corresponds to the reset phase noise. Also, in the signal phase, the signal voltage generated at the sixth node N6 268 corresponds to the reset phase noise and a voltage generated from the light pulses received at the photodiode 202.

Thus, the reset phase noise is cancelled in the subtractor 270, and the sample voltage represent the voltage generated from the light pulses received at the photodiode 202. A flicker noise which is a low frequency noise is introduced because of the operational amplifier 210. During the signal phase, a first sample is taken in between the frame time (T) which corresponds to the first voltage generated at the fourth node N4 266. A second sample is taken at the time equal to the frame time (T) which corresponds to the second voltage generate at the fifth node N5 267. In one example, the first sample is taken at T/2.

The first voltage and the reset voltage provides strong correlation which reduces the flicker noise drastically. In addition, since an average of the first voltage and the second voltage is performed to compute the signal voltage, a thermal noise of the receiver 200 remains unchanged.

A bandwidth of the receiver 200 is computed by multiplication of the resistance and capacitance. Thus, in receiver 200, different samples are acquired at different bandwidths to reduce the flicker noise and to maintain the thermal noise constant. In one embodiment, N resistors are used in the switched resistor network 230 and N capacitors are used in the second switched capacitor network 260, where N is an integer greater than 2.

FIG. 3 illustrates a timing diagram for the receiver 200, according to an embodiment. The timing diagram illustrates the operation of the receiver 200 in the reset phase, the offset phase and the signal phase.

As illustrated, during the reset phase, only the reset switch RS 224 is closed while other switches which include the pixel switch PS 206, the first switch S1 236, the second switch S2 238, the third switch S3 246, the fourth switch S4 252 and the fifth switch S5 254 are opened.

During the offset phase, the reset switch RS 224 is opened and the third switch S3 246 is closed. Other switches which include the pixel switch PS 206, the first switch S1 236, the second switch S2 238, the fourth switch S4 252 and the fifth switch S5 254 remain open. A residual charge is stored in the feedback capacitor CF 222. The residual charge creates a reset voltage at the output port 218 of the operational amplifier 210. This reset voltage is sampled onto the reset capacitor CR 244. Thus, the reset voltage is generated at the third node N3 250.

During the signal phase, in a time period 0 to T/2, the pixel switch PS 206, the first switch S1 236, the fourth switch S4 252 and the fifth switch S5 254 are closed. Other switches which include the reset switch RS 224, the second switch S2 238, the third switch S3 246, the first hold switch H1 248, the second hold switch H2 256, the third hold switch H3 258 are opened.

The second switch S2 238 remains open in all phases. The photodiode 202 generates an input signal in response to the received light pulses. The input signal from the photodiode 202 is received at the first signal capacitor CS1 262 and the second signal capacitor CS2 264 through the second resistor R2 234. A voltage generated at the fourth node N4 266 is a first voltage.

During the signal phase, in a time period T/2 to T, the reset switch RS 224, the first switch S1 236, the second switch S2 238, the third switch S3 246, the fourth switch S4 252, the first hold switch H1 248, the second hold switch H2 256, the third hold switch H3 258 are opened.

The pixel switch PS 206 and the fifth switch S5 254 remain closed such that the input signal from the photodiode 202 is received at the second signal capacitor CS2 264 through the first resistor R1 232 and the second resistor R2 234. A corresponding voltage generated at the fifth node N5 267 is a second voltage.

After the signal phase, the fifth switch S5 254 is opened. The first hold switch H1 248 is closed such that the reset voltage generated at the third node N3 250 is provided to the subtractor 270. The second hold switch H2 256 and the third hold switch H3 258 are closed such that the first voltage and the second voltage are averaged to generate the signal voltage, which is provided to the subtractor 270.

It is understood that the time period 0 to T/2 and T/2 to T is according to an example embodiment to explain the logic flow of operation of the receiver 200 and is understood not to limit the scope of the present disclosure. In one example, the resistance of the first resistor R1 232 and the second resistor R2 234 are equal.

In one version, a capacitance of the first signal capacitor CS1 262 and the second signal capacitor CS2 264 are equal. In another version, a sum of capacitance of the first signal capacitor CS1 262 and the second signal capacitor CS2 264 is equal to a capacitance of the reset capacitor CR 244.

FIG. 4 illustrates a method 400, according to an embodiment. In one version, the method is used in an x-ray system to get rid of a reset phase noise and a flicker noise. The method 400 is explained in connection with the receiver 200 illustrated in FIG. 2. At step 402, a residual charge is stored in a feedback capacitor to generate a reset voltage. For example, the feedback capacitor CF 222 coupled across the operational amplifier 210 stores the residual charge.

At step 404, the reset voltage generated due to the residual charge from the feedback capacitor is sampled onto a reset capacitor through a first resistor and a second resistor such that the reset voltage is generated at a third node coupled to the reset capacitor. In one example, the resistance of the first resistor R1 232 and the second resistor R2 234 are equal. An input signal is generated in response to received light pulses, at step 406. In receiver 200, the photodiode 202 generates an input signal in response to the received light pulses.

At step 408, the input signal is provided through the second resistor to a first signal capacitor and a second signal capacitor such that a first voltage is generated at a fourth node coupled to the first signal capacitor. In one version, a capacitance of the first signal capacitor and the second signal capacitor are equal. In another version, a sum of capacitance of the first signal capacitor and the second signal capacitor is equal to a capacitance of the reset capacitor.

At step 410, the input signal is provided through the first resistor and the second resistor to the second signal capacitor such that a second voltage is generated at a fifth node coupled to the second signal capacitor. The first voltage and the second voltage are averaged to generate a signal voltage, at step 412.

At step 414, the reset voltage is subtracted from the signal voltage to generate a sample voltage. An ADC generates a digital voltage in response to the sample voltage, and a processor processes the digital voltage received from the ADC. The residual charge is because of a reset phase noise in the receiver 200. The reset phase noise is cancelled in the subtractor.

The first voltage and the reset voltage provides strong correlation which reduces the flicker noise drastically. In addition, since an average of the first voltage and the second voltage is performed to compute the signal voltage, a thermal noise of the receiver 200 remains unchanged.

FIG. 5 illustrates a receiver 500, according to an embodiment. The receiver 500 includes a photodiode 502, an operational amplifier 510, a switched resistor network 530, a first switched capacitor network 545, a second switched capacitor network 560, a subtractor 570, an analog to digital converter (ADC) 574 and a processor 580.

A pixel switch PS 506 is coupled to the photodiode 502. The operational amplifier 510 is coupled to the photodiode 502 through the pixel switch PS 506. A feedback capacitor CF 522 and a reset switch RS 524 are coupled between a first input port 512 and an output port 518 of the operational amplifier 510. A second input port 514 of the operational amplifier 510 is coupled to a ground terminal.

The switched resistor network 530 is coupled to the output port 518 of the operational amplifier 510. The switched resistor network 530 includes N resistors illustrated as 532A, 532B, 532C and 532N. A resistance value of these resistors is R/N, R/(N−1), R/(N−2) till R respectively, where N is an integer. For example, when N is equal to 3, the switched resistor network will include 3 resistors of value R/3, R/2 and R.

The N resistors are coupled serially. The switched resistor network includes N first switches illustrates as SA 536A, SB 536B, SC 536C and SN 536N. Each first switch is coupled across each resistor of the N resistors. Each switch is coupled in parallel to each resistor of the N resistors. For example, the first switch SA 536A is couple across the resistor 532A, and the first switch SB 536B is coupled across the resistor 532B.

The first switched capacitor network 545 includes a third switch S3 546 coupled between an output node 542 of the switched resistor network 530 and a third node 550. A reset capacitor CR 544 is coupled to the third switch S3 546 at the third node 550. One end of the reset capacitor CR 544 is coupled to a ground terminal. A first hold switch H1 548 is coupled between the third node 550 and the subtractor 570.

The second switched capacitor network 560 is coupled to the switched resistor network 530. The second switched capacitor network 560 includes N signal capacitor networks illustrated as 560A, 560B, 560C and 560N. Each signal capacitor network includes a fourth switch coupled to an output node 542 of the switched resistor network 530. The fourth switches are illustrated as KA 552A, KB 552B, KC 552C and KN 552N.

Each signal capacitor network also includes a signal capacitor coupled to the fourth switch at a fourth node. One end of the signal capacitor is coupled to a ground terminal. The signal capacitors are illustrates as 562A, 562B, 562C and 562N. A capacitance of each of these signal capacitors is C/N. The signal capacitors are coupled to fourth node illustrated as 566A, 566B, 566C and 566N.

In each signal capacitor network, a second hold switch is coupled between the fourth node and the subtractor 570. The second hold switch are illustrated as LA 556A, LB 556B, LC 556C and LN 556N.

In the signal capacitor network 560A, the fourth switch KA 552A is coupled to the output node 542 of the switched resistor network 530. The signal capacitor 562A is coupled to the fourth switch KA 552A at the fourth node 566A. One end of the signal capacitor 562A is coupled to the ground terminal. The second hold switch LA 556A is coupled between the fourth node 566A and the subtractor 570.

In one version, a sum of capacitance of the signal capacitors is equal to a capacitance of the reset capacitor CR 544. The ADC 574 is coupled to the subtractor 570, and the processor 580 is coupled to the ADC 574. The receiver 500 may include one or more additional components known to those skilled in the relevant art and are not discussed here for simplicity of the description.

The operation of the receiver 500 illustrated in FIG. 5 is explained now. The receiver 500 operates in a reset phase, an offset phase and a signal phase. In the reset phase, the pixel switch PS 506, the third switch S3 546, and the fourth switch (KA 552A, KB 552B, KC 552C and KN 552N) in each signal capacitor network are opened. The reset switch RS 524 is closed.

In the offset phase, the reset switch RS 524 is opened such that a residual charge is stored in the feedback capacitor CF 522. The residual charge creates a reset voltage at the output port 518 of the operational amplifier 510. The pixel switch PS 506, the reset switch RS 524, the N first switches (SA 536A, SB 536B, SC 536C and SN 536N), and the fourth switch (KA 552A, KB 552B, KC 552C and KN 552N) in each signal capacitor network remain open while the third switch S3 546 is closed.

The reset voltage generated by the residual charge on the feedback capacitor CF 522 is sampled onto the reset capacitor CR 544. Thus, the reset voltage is generated at the third node 550. The photodiode 502 generates an input signal in response to received light pulses. In the signal phase, for every time period equal to time (T) divided by N, the reset switch RS 524, the third switch S3 546, the first hold switch H1 548, and the second hold switch (LA 556A, LB 556B, LC 556C and LN 556N) in each signal capacitor network are opened.

The pixel switch PS 506 is closed such that the input signal from the photodiode 502 is received in the switched resistor network 530 and the second switched capacitor network 560. For every time period equal to T/N, one first switch is opened and (N−1) first switches are closed such that an effective resistance is provided by the switched resistor network 530.

In addition, a set of fourth switches in the second switched capacitor network 560 are closed such that an effective capacitance is provided by the second switched capacitor network 560. A bandwidth of the receiver is proportional to the effective resistance and the effective capacitance.

This is illustrated for N equal to 3. The switched resistor network 530 will have 3 resistors of resistance values R/3, R/2 and R. The second switched capacitor network 560 will have 3 signal capacitor networks and a capacitance of each signal capacitor in each signal capacitor network will be C/3. In the signal phase, the receiver 500 will have three time periods of T/3. In the first time period of T/3, a first switch is opened and two first switches are closed. Thus, the second switched capacitor network 560 receives the input signal from the photodiode 502 through the resistance R/3. R/3 is the effective resistance provided by the switched resistor network 530. Also, the fourth switch in each signal capacitor network is closed. Thus, the effective capacitance provided by the second switched capacitor network 560 is C (3*C/3). A bandwidth of the receiver 500 in the first time period of T/3 is defined as:

$$BW = \frac{1}{\left(\frac{R}{3}\right)C} = \frac{3}{RC} \quad (1)$$

In the next time period of T/3, the second switched capacitor network 560 receives the input signal from the photodiode 502 through the resistance R/2. R/2 is the effective resistance provided by the switched resistor network 530. Also, one fourth switch is opened while two fourth switches are closed. Thus, the effective capacitance provided by the second switched capacitor network 560 is (C−C/3). A bandwidth of the receiver 500 in the second time period of T/3 is defined as:

$$BW = \frac{1}{\left(\frac{R}{2}\right)\left(C - \frac{C}{3}\right)} = \frac{3}{RC} \quad (2)$$

In the next time period of T/3, the second switched capacitor network 560 receives the input signal from the photodiode 502 through the resistance R. R is the effective resistance provided by the switched resistor network 530. Also, two fourth switches are opened while one fourth switch is closed. Thus, the effective capacitance provided by the second switched capacitor network 560 is (C−2C/3). A bandwidth of the receiver 500 in the third time period of T/3 is defined as:

$$BW = \frac{1}{R*\left(C - \frac{2C}{3}\right)} = \frac{3}{RC} \quad (3)$$

During each time period of T/3, the signal capacitors receive the input signal from the photodiode 502 and a corresponding voltage is generated at the respective fourth nodes (566A, 566B, 566C and 566N).

After the signal phase, the third switch S3 546, the fourth switch (KA 552A, KB 552B, KC 552C and KN 552N) in each signal capacitor are opened. The first hold switch H1 548 is closed such that the reset voltage is provided to the subtractor 570. The second hold switch (LA 556A, LB 556B, LC 556C and LN 556N) in each signal capacitor network are closed such that the voltage at the respective fourth nodes are averaged to generate the signal voltage.

Therefore, the first switched capacitor network 545 samples the reset voltage, and the second switched capacitor network 560 samples the signal voltage. The subtractor 570 receives the reset voltage and the signal voltage, and generates a sample voltage. In one example, the subtractor 570 subtracts the reset voltage from the signal voltage and generates the sample voltage. The ADC 574 generates a digital voltage in response to the sample voltage, and the processor 580 processes the digital voltage received from the ADC 574.

The residual charge stored during the offset phase is because of reset phase noise in the receiver 500. The receiver 500 is reset before a start of each frame. A frame spans for a frame time (T). This introduces the reset phase noise in the receiver 500. However, in the offset phase, the reset voltage generated at the third node 550 corresponds to the reset phase noise. Also, in the signal phase, the signal voltage generated by the second switched capacitor network 560 corresponds to the reset phase noise and a voltage generated from the light pulses received at the photodiode 502.

Thus, the reset phase noise is cancelled in the subtractor 570, and the sample voltage represent the voltage generated from the light pulses received at the photodiode 502. A flicker noise which is a low frequency noise is introduced because of the operational amplifier 510. During the signal phase, samples at taken at intervals T/N (for example T/3) and the corresponding voltages generated at the respective fourth nodes is averaged to compute the signal voltage.

This reduces the flicker noise drastically. The bandwidth of the receiver 500 is computed by multiplication of the resistance and capacitance. Thus, in receiver 500, different samples are acquired at different bandwidths to reduce the flicker noise and to maintain the thermal noise constant.

FIG. 6 illustrates an x-ray system 600, according to an embodiment. The x-ray system 600 includes an x-ray source 602. The x-ray source 602 generates x-rays. An object 604 receives the x-rays from the x-ray source 602. The x-rays pass through the object 604. The object 604 is any entity of interest which may include, but not limited to, a human, an automated component, an animal, a device etc.

A scintillator 606 generates light pulses is response to the x-rays received from the object 604. An analog front end (AFE) array receives the light pulses from the scintillator 606. The AFE array includes a plurality of receivers. At least one receiver of the plurality of receives is analogous to the receiver 200 or the receiver 500 in connections and operation.

The reset phase noise is cancelled in the receiver. As multiple samples are taken in between a frame time (T), a strong correlation between the samples reduces the flicker noise drastically. In addition, since an average of the voltage samples is performed, a thermal noise of the receiver remains unchanged. In the receiver, different samples are acquired at different bandwidths to reduce the flicker noise and to maintain the thermal noise constant.

The foregoing description sets forth numerous specific details to convey a thorough understanding of the invention. However, it will be apparent to one skilled in the art that the invention may be practiced without these specific details. Well-known features are sometimes not described in detail in order to avoid obscuring the invention. Other variations and embodiments are possible in light of above teachings, and it is thus intended that the scope of invention not be limited by this Detailed Description, but only by the following Claims.

The invention claimed is:

1. A receiver comprising:
    a photodiode configured to generate an input signal in response to received light pulses;
    a pixel switch coupled to the photodiode;
    an operational amplifier coupled to the photodiode through the pixel switch;

a feedback capacitor and a reset switch coupled between a first input port and an output port of the operational amplifier;

a switched resistor network coupled to the output port of the operational amplifier;

a first switched capacitor network coupled to the switched resistor network and configured to sample a reset voltage;

a second switched capacitor network coupled to the switched resistor network and configured to sample a signal voltage; and a subtractor configured to receive the reset voltage and the signal voltage, and configured to generate a sample voltage, wherein the second switched capacitor network comprises two or more capacitors.

2. The receiver of claim 1 further comprising:
an analog to digital converter (ADC) coupled to the subtractor, and configured to generate a digital voltage in response to the sample voltage; and
a processor coupled to the ADC, and configured to process the digital voltage.

3. The receiver of claim 1, wherein the switched resistor network comprises:
a first resistor coupled between the output port of the operational amplifier and a first node;
a second resistor coupled between the first node and a second node, the second resistor being coupled to the first resistor at the first node serially;
a first switch coupled in parallel to the first resistor between the output port of the operational amplifier and the first node; and
a second switch coupled in parallel to the second resistor between the first node and the second node.

4. The receiver of claim 3, wherein the first switched capacitor network comprises:
a third switch coupled between the second node and a third node;
a reset capacitor coupled to the third switch at the third node, wherein one end of the reset capacitor is coupled to a ground terminal; and
a first hold switch coupled between the third node and the subtractor.

5. The receiver of claim 4, wherein the second switched capacitor network comprises:
a fourth switch coupled between the second node and a fourth node;
a first signal capacitor coupled to the fourth switch at the fourth node, wherein one end of the first signal capacitor is coupled to the ground terminal;
a fifth switch coupled between the second node and a fifth node,
a second signal capacitor coupled to the fifth switch at the fifth node, wherein one end of the second signal capacitor is coupled to the ground terminal;
a second hold switch coupled between the fourth node and a sixth node; and
a third hold switch coupled between the fifth node and the sixth node.

6. The receiver of claim 5, wherein the subtractor is coupled to the third node and the sixth node, and the subtractor is configured to subtract the reset voltage generated at the third node from the signal voltage generated at the sixth node.

7. The receiver of claim 6, wherein the receiver is configured to operate in a reset phase, an offset phase and a signal phase.

8. The receiver of claim 7, wherein in the reset phase:
the pixel switch, the third switch, the fourth switch and the fifth switch are opened; and
the reset switch is closed.

9. The receiver of claim 7, wherein in the offset phase:
the reset switch is opened such that a residual charge is stored in the feedback capacitor, wherein the residual charge generates the reset voltage at the output port of the operational amplifier;
the pixel switch, the reset switch, the first switch, the second switch, the first hold switch, the fourth switch and the fifth switch are opened; and
the third switch is closed such that the reset voltage is sampled onto the reset capacitor, and the reset voltage is generated at the third node.

10. The receiver of claim 7, wherein in the signal phase:
the reset switch, the second switch, the third switch, the first hold switch, the second hold switch and the third hold switch are opened;
the pixel switch, the first switch, the fourth switch and the fifth switch are closed such that the input signal from the photodiode is received at the first signal capacitor and the second signal capacitor through the second resistor, and a corresponding voltage generated at the fourth node is a first voltage;
the reset switch, the first switch, the second switch, the third switch, the first hold switch, the fourth switch, the second hold switch and the third hold switch are opened; and
the pixel switch and the fifth switch are closed such that the input signal from the photodiode is received at the second signal capacitor through the first resistor and the second resistor, and a corresponding voltage generated at the fifth node is a second voltage.

11. The receiver of claim 10, wherein after the signal phase:
the third switch, the fourth switch and the fifth switch are opened;
the first hold switch is closed such that the reset voltage generated at the third node is provided to the subtractor; and
the second hold switch and the third hold switch are closed such that the signal voltage generated at the sixth node is an average of the first voltage and the second voltage.

12. The receiver of claim 5, wherein a resistance of the first resistor and the second resistor are equal, and a capacitance of the first signal capacitor and the second signal capacitor are equal.

13. The receiver of claim 5, wherein a sum of capacitance of the first signal capacitor and the second signal capacitor is equal to a capacitance of the reset capacitor.

14. A method comprising:
storing a residual charge in a feedback capacitor to generate a reset voltage;
sampling the reset voltage onto a reset capacitor through a first resistor and a second resistor such that the reset voltage is generated at a first node coupled to the reset capacitor;
generating an input signal in response to received light pulses;
providing the input signal through the second resistor to a first signal capacitor and a second signal capacitor such that a first voltage is generated at a second node coupled to the first signal capacitor;
providing the input signal through the first resistor and the second resistor to the second signal capacitor such that a second voltage is generated at a third node coupled to the second signal capacitor;
averaging the first voltage and the second voltage to generate a signal voltage; and
subtracting the reset voltage from the signal voltage to generate a sample voltage.

15. The method of claim 14 further comprising:
generating a digital voltage from the sample voltage; and
processing the digital voltage.

16. The method of claim 14, wherein a resistance of the first resistor and the second resistor are equal, and a capacitance of the first signal capacitor and the second signal capacitor are equal.

17. The method of claim 14, wherein a sum of capacitance of the first signal capacitor and the second signal capacitor is equal to a capacitance of the reset capacitor.

18. A receiver comprising:
a photodiode configured to generate an input signal in response to received light pulses in a frame time;
a pixel switch coupled to the photodiode;
an operational amplifier coupled to the photodiode through the pixel switch;
a feedback capacitor and a reset switch coupled between a first input port and an output port of the operational amplifier;
a switched resistor network coupled to the output port of the operational amplifier, the switched resistor network comprising N resistors, where N is an integer greater than or equal to two;
a first switched capacitor network coupled to the switched resistor network and configured to sample a reset voltage;
a second switched capacitor network coupled to the switched resistor network and configured to sample a signal voltage; and
a subtractor configured to receive the reset voltage and the signal voltage, and configured to generate a sample voltage, wherein the second switched capacitor network comprises N capacitors.

19. The receiver of claim 18, wherein the switched resistor network comprises N first switches, each first switch is coupled across each resistor of the N resistors, wherein the N resistors are coupled serially.

20. The receiver of claim 19, wherein the first switched capacitor network comprises:
a third switch coupled between an output node of the switched resistor network and a third node;
a reset capacitor coupled to the third switch at the third node, wherein one end of the reset capacitor is coupled to a ground terminal; and
a first hold switch coupled between the third node and the subtractor.

21. The receiver of claim 20, wherein the second switched capacitor network comprises N signal capacitor networks, each signal capacitor network comprising:
a fourth switch coupled to the output node of the switched resistor network;
a signal capacitor coupled to the fourth switch at a fourth node, wherein one end of the signal capacitor is coupled to a ground terminal; and
a second hold switch coupled between the fourth node and the subtractor.

22. The receiver of claim 21, wherein the receiver is configured to operate in a reset phase, an offset phase and a signal phase.

23. The receiver of claim 22, wherein in the reset phase:
the pixel switch, the third switch, and the fourth switch in each signal capacitor network are opened; and
the reset switch is closed.

24. The receiver of claim 22, wherein in the offset phase:
the reset switch is opened such that a residual charge is stored in the feedback capacitor, wherein the residual charge generates the reset voltage at the output port of the operational amplifier;
the pixel switch, the reset switch, the N first switches, the first hold switch, and the fourth switch in each signal capacitor network are opened; and
the third switch is closed such that the reset voltage is sampled onto the reset capacitor, and the reset voltage is generated at the third node.

25. The receiver of claim 22, wherein in the signal phase for every time period equal to the frame time divided by N:
the reset switch, the third switch, the first hold switch, and the second hold switch in each signal capacitor network are opened;
the pixel switch is closed such that the input signal from the photodiode is received in the switched resistor network and the second switched capacitor network;
one first switch is opened and (N−1) first switches are closed such that an effective resistance is provided by the switched resistor network; and
a set of fourth switches in the second switched capacitor network are closed such that an effective capacitance is provided by the second switched capacitor network, wherein a bandwidth of the receiver is proportional to the effective resistance and the effective capacitance.

26. An x-ray system comprising:
an x-ray source configured to generate x-rays;
a scintillator configured to generate light pulses in response to the x-rays; and
an analog front end (AFE) array configured to receive the light pulses, the AFE array comprising a plurality of receivers, and at least one receiver of the plurality of receivers comprising:
a photodiode configured to generate an input signal in response to received light pulses,
a pixel switch coupled to the photodiode;
an operational amplifier coupled to the photodiode through the pixel switch;
a feedback capacitor and a reset switch coupled between a first input port and an output port of the operational amplifier;
a switched resistor network coupled to the output port of the operational amplifier;
a first switched capacitor network coupled to the switched resistor network and configured to sample a reset voltage;
a second switched capacitor network coupled to the switched resistor network and configured to sample a signal voltage; and
a subtractor configured to receive the reset voltage and the signal voltage, and configured to generate a sample voltage, wherein the second switched network comprises two or more capacitors.

* * * * *